(12) United States Patent
Fukuda et al.

(10) Patent No.: US 8,375,772 B2
(45) Date of Patent: Feb. 19, 2013

(54) LIQUID CHROMATOGRAPHY APPARATUS AND LIQUID CHROMATOGRAPHY ANALYSIS METHOD

(75) Inventors: Masato Fukuda, Hitachinaka (JP); Hiroyuki Wada, Hitachinaka (JP); Masahito Ito, Hitachinaka (JP); Hironori Kaji, Hitachinaka (JP); Kosaku Toyosaki, Ishioka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 601 days.

(21) Appl. No.: 12/244,846

(22) Filed: Oct. 3, 2008

(65) Prior Publication Data

US 2009/0090173 A1    Apr. 9, 2009

(30) Foreign Application Priority Data

Oct. 3, 2007   (JP) .................................. 2007-259322

(51) Int. Cl.
  *G01N 30/04*    (2006.01)
(52) U.S. Cl. ...................................... 73/61.55; 73/53.01
(58) Field of Classification Search .................. 73/61.55, 73/53.01
  See application file for complete search history.

(56) References Cited

U.S. PATENT DOCUMENTS

| | | | | |
|---|---|---|---|---|
| 4,311,586 A | * | 1/1982 | Baldwin et al. | 210/101 |
| 4,422,942 A | * | 12/1983 | Allington | 210/659 |
| 4,769,153 A | * | 9/1988 | Allington | 210/656 |
| 4,781,824 A | * | 11/1988 | Allington | 210/101 |
| 4,882,781 A | * | 11/1989 | Allington | 700/282 |
| 5,040,126 A | * | 8/1991 | Allington | 702/47 |
| 6,260,407 B1 | * | 7/2001 | Petro et al. | 73/61.52 |
| 6,475,391 B2 | * | 11/2002 | Safir et al. | 506/12 |
| 6,561,767 B2 | * | 5/2003 | Berger et al. | 417/53 |
| 6,584,832 B2 | * | 7/2003 | Petro et al. | 506/12 |
| 6,976,383 B2 | * | 12/2005 | Petro et al. | 73/61.55 |
| 2002/0116989 A1 | * | 8/2002 | Davison et al. | 73/61.55 |
| 2004/0018099 A1 | * | 1/2004 | Berger et al. | 417/313 |

FOREIGN PATENT DOCUMENTS

| | | |
|---|---|---|
| JP | 3491948 | 11/2003 |
| JP | 3709409 | 8/2005 |
| JP | 2006-017590 | 1/2006 |
| WO | WO 03/079000 A1 | 9/2003 |

\* cited by examiner

*Primary Examiner* — Lisa Caputo
*Assistant Examiner* — Rodney T Frank
(74) *Attorney, Agent, or Firm* — Antonelli, Terry, Stout & Kraus, LLP.

(57) ABSTRACT

An object of the present invention is to improve the accuracy in analysis repeatability of a liquid chromatography apparatus that feeds different eluent by use of a plurality of pumps and achieves the mixture of eluent.

Each of the pumps includes means for notifying an automatic sampler and a higher-level control unit that the specified timing of a liquid feeding cycle is reached. A pump whose liquid feeding cycle is the slowest transmits own information so that analysis is synchronized with a liquid feeding cycle. Moreover, a cycle position of a liquid feeding cycle at the end of analysis is expected, and the analysis time is automatically adjusted so that the wait time until the start of the next analysis becomes the shortest.

10 Claims, 17 Drawing Sheets

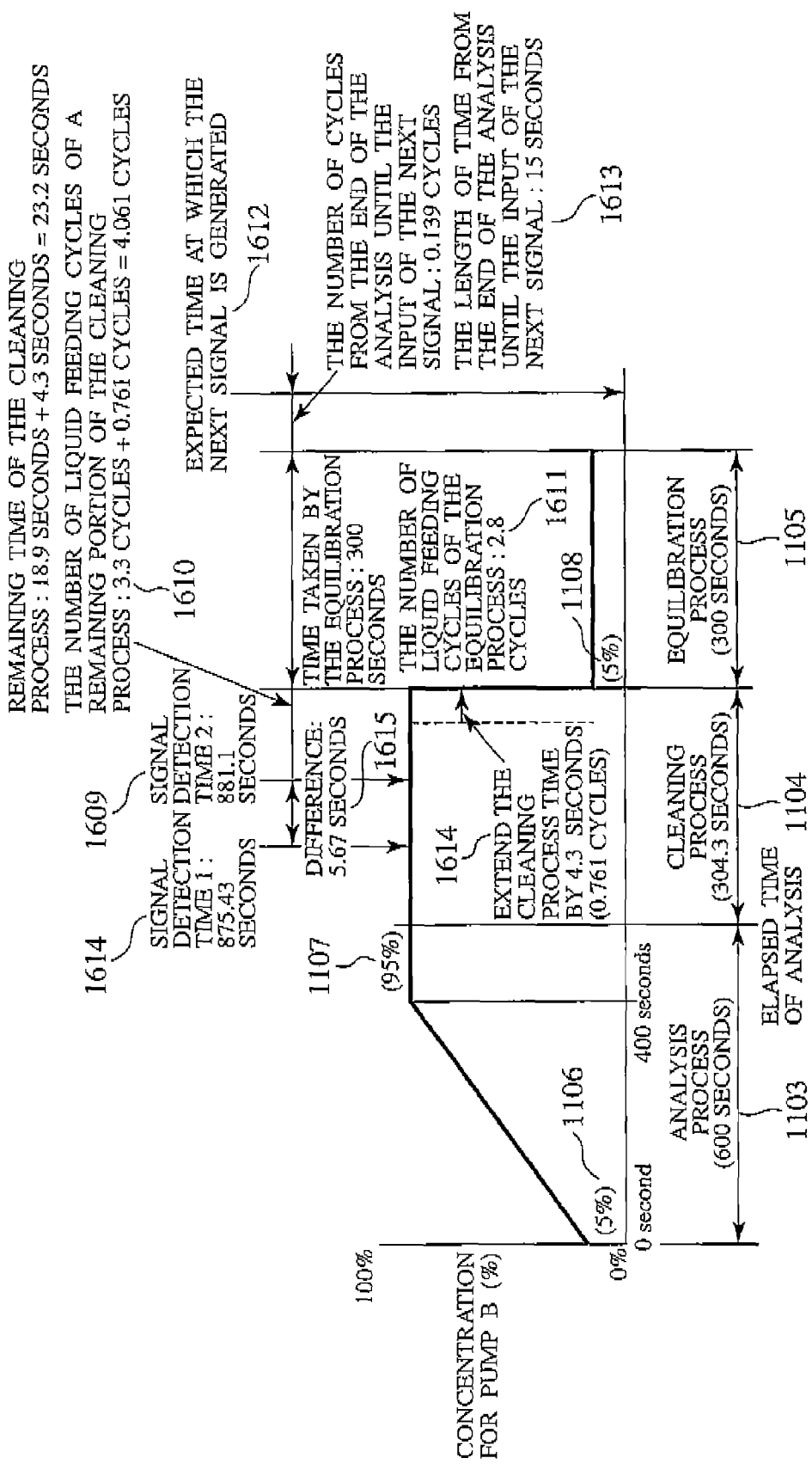

FIG.17

TIME TABLE BEFORE THE CORRECTION
OF THE ANALYSIS TIME

1102:

| TIME (sec) | CONCENTRATION FOR PUMP A (%) | CONCENTRATION FOR PUMP B (%) | PROCESS |
|---|---|---|---|
| 0.0 | 95 | 5 | ANALYSIS PROCESS 1103 |
| 400.0 | 5 | 95 | |
| 600.0 | 5 | 95 | |
| 600.0 | 5 | 95 | CLEANING PROCESS 1104 |
| 900.0 | 5 | 95 | |
| 900.0 | 95 | 5 | EQUILIBRATION PROCESS 1105 |
| 1200.0 | 95 | 5 | |

⇓

TIME TABLE AFTER THE CORRECTION
OF THE ANALYSIS TIME

1702:

| TIME (sec) | CONCENTRATION FOR PUMP A (%) | CONCENTRATION FOR PUMP B (%) | PROCESS |
|---|---|---|---|
| 0.0 | 95 | 5 | ANALYSIS PROCESS 1103 |
| 400.0 | 5 | 95 | |
| 600.0 | 5 | 95 | |
| 600.0 | 5 | 95 | CLEANING PROCESS 1104 |
| 904.3 | 5 | 95 | |
| 904.3 | 95 | 5 | EQUILIBRATION PROCESS 1105 |
| 1204.3 | 95 | 5 | |

1703

LIQUID CHROMATOGRAPHY APPARATUS AND LIQUID CHROMATOGRAPHY ANALYSIS METHOD

BACKGROUND OF THE INVENTION

1. Field of the Invention

The present invention relates to a liquid chromatography apparatus and a liquid chromatography analysis method.

2. Description of the Related Art

When analysis is performed by use of a liquid chromatography apparatus, a plurality of constituents are accurately detected in a short period of time by mixing a plurality of eluents, and then by changing the concentration thereof during the analysis (gradient). This is a mainly used method. According to the method for mixing the eluents, a plurality of pumps, each of which differs in liquid feeding speed, are used to achieve the target mixture concentration on the basis of the difference in liquid feeding speed among the pumps. Such a method has come into widespread use because the mixture concentration can be quickly changed and the mixture concentration can be set with high accuracy.

JP-A-2006-17590, Japanese Patent Nos. 3491948 3709409 are disclosed as documents relating to the above.

SUMMARY OF THE INVENTION

When a pump continuously feeds liquid for a long time, the pump is inevitably required to carry out both a process for sucking eluent and a process for discharging the eluent. Ideally, also the liquid feeding at a portion between the processes must be constantly controlled. However, in actuality, a change in liquid feeding amount will cause problems such as detection noises and variations in mixture ratio.

In order to minimize the change as described above, for example, two syringes are used to perform such control that a sucking process and a discharging process are reversed to feed liquid as specified. However, at present, the use of such a control is far from complete elimination of the noises.

When measurements which require the analysis repeatability with high accuracy are made, the timing at which the noises occur during analysis, and the number of times the noises have occurred, are important elements in terms of repeatability.

Moreover, in the method in which eluent is fed and mixed by use of a plurality of pumps, it is known that noises caused by a pump whose liquid feeding cycle is faster are easily absorbed and smoothed by a liquid mixing mechanism (mixer), whereas noises caused by a pump whose liquid feeding cycle is slower are neither absorbed nor smoothed but directly influence the analysis repeatability just as they are.

One of objects of the present invention is to increase the analysis repeatability of a liquid chromatograph.

One feature of the present invention is that in a liquid chromatography apparatus including a sample syringe and a plurality of pumps, the sample injection operation is synchronized with a phase of a control process for a pump whose flow speed at the time of sample injection is slow. A more preferable liquid chromatography apparatus, which includes a sample syringe, and a plurality of pumps, is so configured that when the flow speed of at least one pump differs from that of the other pumps, the sample injection operation is synchronized with a phase of a control process for a pump whose flow speed at the time of sample injection is slowest.

One and other features of the present invention will be further described as below.

According to the present invention, for example, the analysis repeatability of liquid chromatograph can be improved.

BRIEF DESCRIPTION OF THE DRAWINGS

Other objects and advantages of the invention will become apparent from the following description of embodiments with reference to the accompanying drawings in which;

FIG. 16 is a chart illustrating an example of a liquid feeding process after the analysis time is corrected by the pressurization/acceleration control correction processing according to the embodiment of the present invention; and FIG. 17 illustrates an example of a time table after the analysis time is corrected by the pressurization/acceleration control correction processing according to the embodiment of the present invention.

DESCRIPTION OF THE PREFERRED EMBODIMENTS

Figure 1:
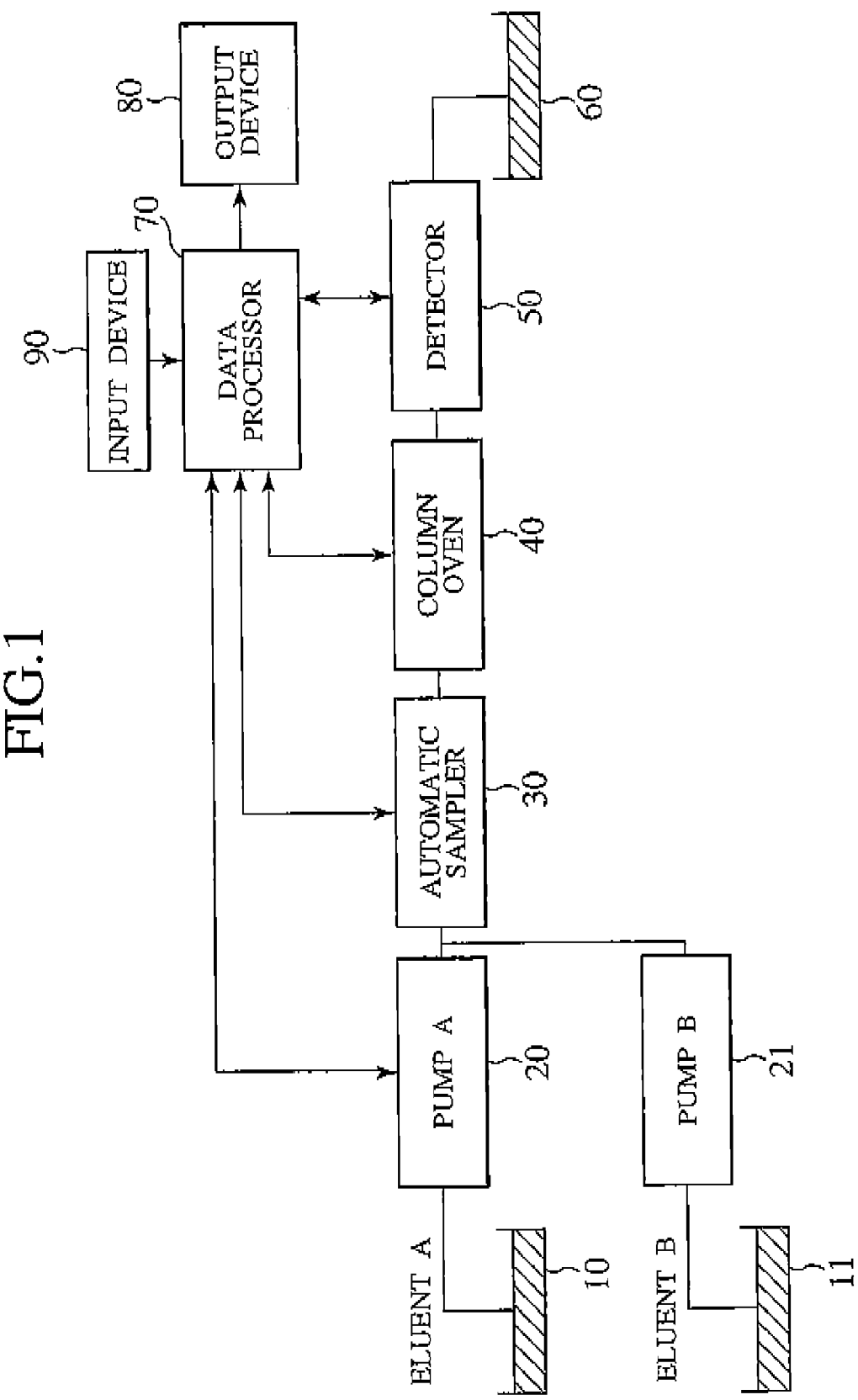
FIG. 1 is a diagram illustrating as an example the configuration of a liquid chromatography apparatus that mixes eluent by use of a plurality of pumps according to an embodiment of the present invention.

An object to be achieved in the embodiments of the present invention is to keep the influence of noises of a pump between analyses constant, thereby improving the analysis repeatability. This object is achieved by causing noises of a pump whose liquid feeding cycle is slow to occur by the same number of times and in the same timing, during one analysis.

Next, two problems are solved which will be caused by synchronizing the analysis with a liquid feeding cycle of a slow pump whose liquid feeding cycle is slow.

The first problem is diffusion of samples. The diffusion occurs when operation is waiting for synchronization with a slow pump with a sample sucked into a thin injection flow path (nozzle). If the sample is kept in this state for a long period of time, the sample diffuses in the nozzle, which exerts a bad influence on the repeatability of the analysis.

The second problem is the time it takes for measurements. More specifically, there is a possibility that the synchronization with a liquid feeding cycle of the slow pump will require a very long period of time for measurements when analysis is performed a plurality of times. This is a disadvantage for the performance of a liquid chromatography apparatus.

According to the embodiments of the present invention, as means for solving the problems, each of a plurality of pumps, each of which achieves the mixed concentration, is provided with means for notifying an automatic sampler and a higher-level control unit that the specified timing of a liquid feeding cycle has reached.

This means is implemented by a hardware-based electric signal, software-based communication means, or the like. Among the plurality of pumps, a pump which judges the liquid feeding cycle thereof to be the slowest uses this notification means to notify the automatic sampler and the higher-level control unit of the information about the judgment, and thereby instructs the automatic sampler and the higher-level control unit to start the analysis. In this manner, the start of the analysis of the plurality of pumps including the pump whose liquid feeding cycle is the slowest is synchronized with one another.

This makes it possible to cause noises of a pump whose liquid feeding cycle is slow to occur by the same number of times and in the same timing during one analysis.

Examples of a judgment method by which a pump judges an analysis cycle thereof to be the slowest include a method in which a pump is notified by a higher-level control unit that the analysis cycle of the pump is the slowest. In addition, there is also such judgment means that each pump includes information about a plurality of pumps each achieving the concentration, and that each pump makes a judgment from the information as to whether or not its own analysis cycle is the slowest among the plurality of pumps.

In order to prevent a sample from being kept sucked into a nozzle for a long period of time, a period of time from the operation of sucking the sample into the nozzle until the injection operation is kept short as specified.

For that purpose, a synchronization signal, which is synchronized with the slow pump, is used as a start signal that instructs the start of the operation of sucking the sample into the nozzle.

This synchronization signal can also be used as an advance notice signal notifying in advance that a sample will be injected into a measurement flow path. Accordingly, the injection can be synchronized with the pump by injecting the sample into the measurement flow path after a lapse of the specified length of time (for example, after specified seconds) since the receipt of the synchronization signal.

For a pump whose liquid feeding cycle is slow, a cycle position of a liquid feeding cycle at the end of analysis is expected by calculating or measuring the operating time at the certain mixture concentration; and the analysis time is automatically adjusted so that the wait time until the start of the next analysis becomes the shortest. Thus, the number of processes of the liquid feeding cycle in the analysis is kept specific, which makes it possible to achieve the automatic optimization of the measuring time.

In a gradient in which the concentration mixing ratio is changed during the analysis, the time is automatically adjusted in such timing that the liquid feeding speed of the slowest pump at the time of sample injection becomes the highest during the analysis. This makes it possible to minimize the influence on the analysis time, thereby achieving the automatic optimization of the measuring time.

An analysis is made in synchronization with a pump whose liquid feeding cycle is the slowest so as to cause noises of the pump whose liquid feeding cycle is slow to occur by the same number of times and in the same timing in one analysis This makes it possible to relatively eliminate the influence of the noises of the pump between analyses. Therefore, the analysis repeatability can be achieved with high accuracy; and quantitative and identification values of a material in the analysis can be controlled such that the quantitative and identification values become closer to their true values.

By use of a method for automatically optimizing the measuring time in synchronization with a pump whose liquid feeding cycle is slow, it becomes possible to achieve both an improvement in accuracy of analysis and a reduction in measuring time, which are required for a liquid chromatography apparatus.

Embodiments of the present invention will be described in detail below with reference to accompanying drawings.

For the best understanding of the embodiments of the present invention, a liquid chromatography apparatus shown in FIG. 1 is taken as an example. The liquid chromatography apparatus includes: a chromatography unit including a pump A, a pump B, an automatic sampler, a column oven, and a detector; and a data processor for controlling a chromatography unit.

First Embodiment

The configuration of a liquid chromatography apparatus according to this embodiment will be described with reference to FIG. 1. Eluent A 10 and B 11 are sucked by pumps A 20 and B 21 respectively. After the eluent A 10 and B 11 are mixed, the eluent A 10 and B 11 are fed into a column oven 40 through an automatic sampler 30. The pumps A20 and B21 are controlled by a data processor 70. Mixed liquid of the eluent fed by the pumps A 20 and B 21 transfers a sample injected by the automatic sampler 30 to the column oven 40 so that the sample is transferred to the column oven 40 together with the eluent. The column oven 40 separates the sample on a constituent basis. The column oven includes a separation column whose temperature is kept constant with an oven.

Each of the separated constituents is detected by a detector 50, and is then disposed of in a waste liquid container 60. A measurement value of each constituent detected by the detector 50 is inputted into the data processor 70 where the peak height and area of the chromatography are calculated. The result of the calculation is output to an output device 80 including, for example, a display unit and a printer.

An input device 90 including a keyboard and a mouse is connected to the data processor 70. The input device 90 is used to input settings of device configuration information, and to input settings of analysis conditions. In addition, the data processor 70 controls the automatic sampler 30 to control the quantity of the sample to be injected and the temperature of the column oven 40.

The pumps A 20 and B 21 (liquid feeding apparatuses) will be described with reference to FIG. 2. The liquid feeding unit shown in FIG. 2 includes a first cylinder 202 in which a first plunger 201 is built; and a second cylinder 204 in which a second plunger 203 is built. The first and second plungers 201 and 203 included in the first and second cylinders 202 and 204 are reciprocated by first and second cams 205 and 206 respectively. These cams 205 and 206 are driven for rotation by a motor 207. The motor 207 is controlled by a control unit 208.

The first cylinder 202 is provided with an entrance check valve 209 and an exit check valve 210 at the entrance and exit thereof. Eluent 211 is sucked from the intake side of the entrance check valve 209. Further, the liquid feeding unit includes a cylinder pressure detector 212 for measuring the internal pressure of the first cylinder 202, and a discharge pressure detector 213 for detecting the discharge pressure.

In addition, a disk member 214 provided with a slit is secured to a rotating shaft such that a cam position detection sensor 215 detects a cam position. A flow path for supplying the eluent 211, to the entrance side of the first cylinder 202, from the supply source side on which the eluent 211 accumulates is called "supply flow path". This supply flow path is provided with the entrance check valve 209. A flow path for introducing eluent, which is discharged from the discharge side of the first cylinder 202, into the entrance side of the second cylinder 204 is called "intermediate flow path". The intermediate flow path is provided with the exit check valve 210.

Figure 2:
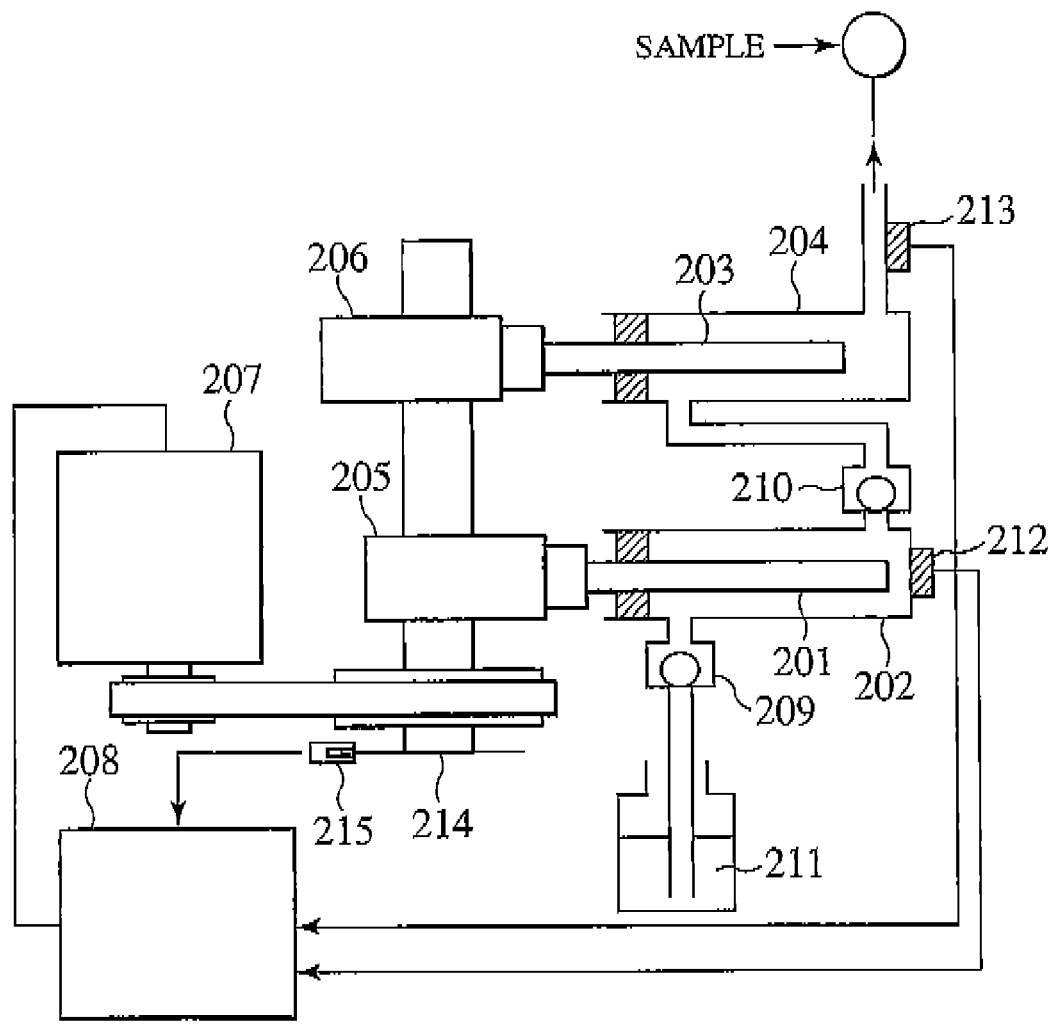
FIG. 2 is a diagram illustrating as an example the structure of a pump (liquid feeding unit) according to an embodiment of the present invention.

The pump shown in FIG. 2 has such a mechanism that the rotation of the first and second cams 205 and 206 by one turn causes the first and second plungers 201 and 203 to make one reciprocating motion which corresponds to one sucking and discharge cycle. Because the capacity of the first cylinder 202 is the same as that of the second cylinder 204, a flow rate fed in one sucking and discharge cycle is constant.

Accordingly, control for changing the liquid feeding amount using the pump shown in FIG. 2 is performed by controlling the rotational speed of the motor 207 so as to change the rotational speed of the first and second cams 205 and 206.

By use of the pumps A 20 and B 21 shown in FIG. 1, which are based on the liquid feeding unit shown in FIG. 2, the eluent A 10 is mixed with the eluent B 11 at the target concentration by changing the cam rotational speed of each of the pumps A 20 and B 21. Such mixture operation is controlled as follows.

Here, the control is based on the assumptions: one turn of the cam of the pump shown in FIG. 2 causes sucking and discharging whose amount corresponds to 100 μL; the liquid feeding amount required for analysis is 1000 μL/min; and a ratio of the eluent A 10 to the eluent B 11 is equivalent to 95% to 5%.

On the assumption that 10 turns per minute is required as the liquid feeding amount, in order to rotate the cam of each of the pumps A 20 and B 21 on the basis of a ratio of concentration of the eluent A 10 to the eluent B 11, the rotational speed of the motor is controlled so that the cam of the pump A 20 rotates by 9.5 turns per minute whereas the cam of the pump B 21 rotates 0.5 turns per minute.

If the above values are compared with each other based on one sucking and discharge cycle of the pump B 21 that is the slower pump, the cam of the pump A 20 rotates by 19 turns while the cam of the pump B 21 rotates by one turn for 2 minutes.

Figure 3:
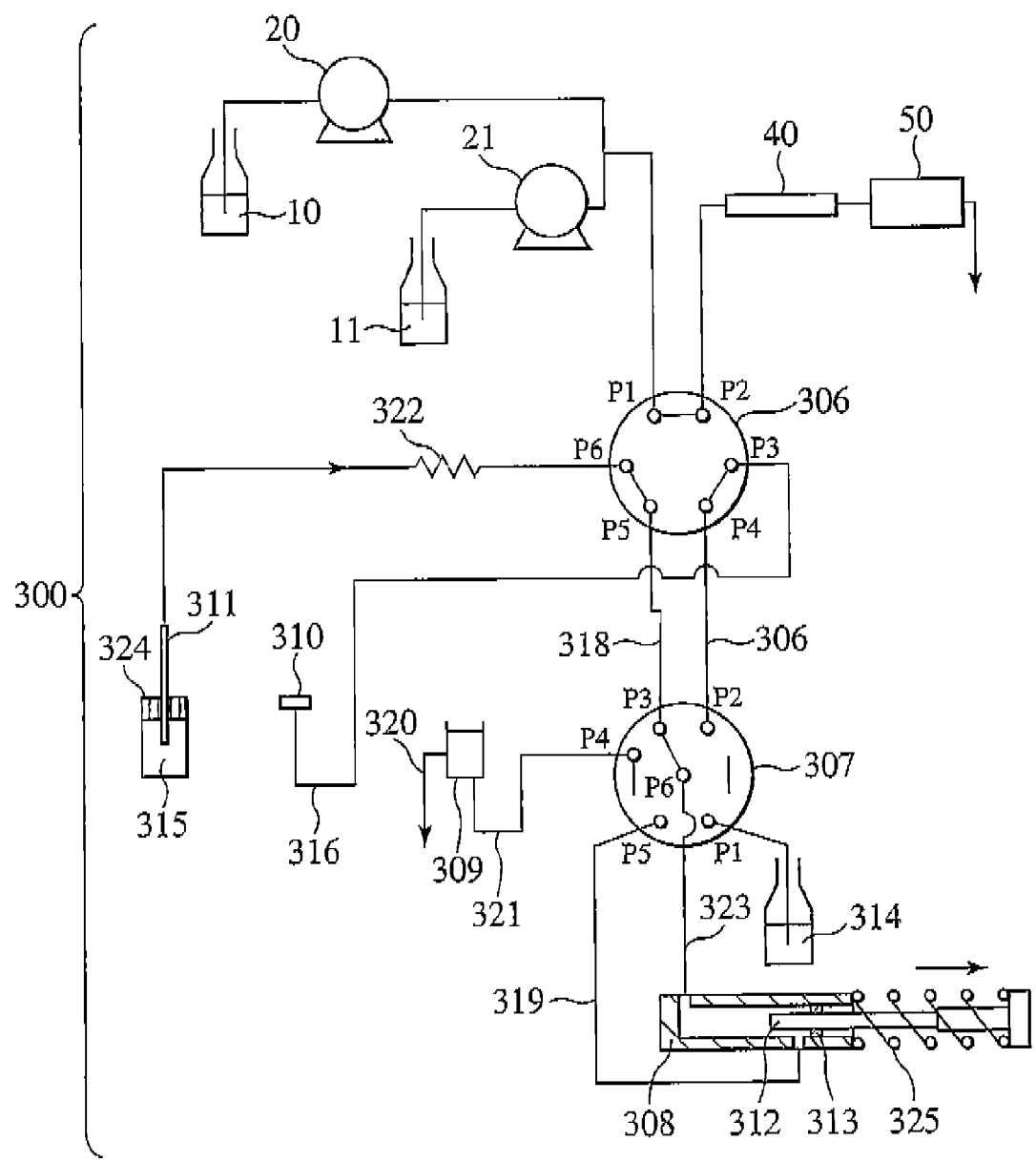
FIG. 3 is a diagram illustrating the structure of an automatic sampler and an example of the mechanical system operation thereof (at the time of sucking a sample) according to an embodiment of the present invention.
Figure 4:
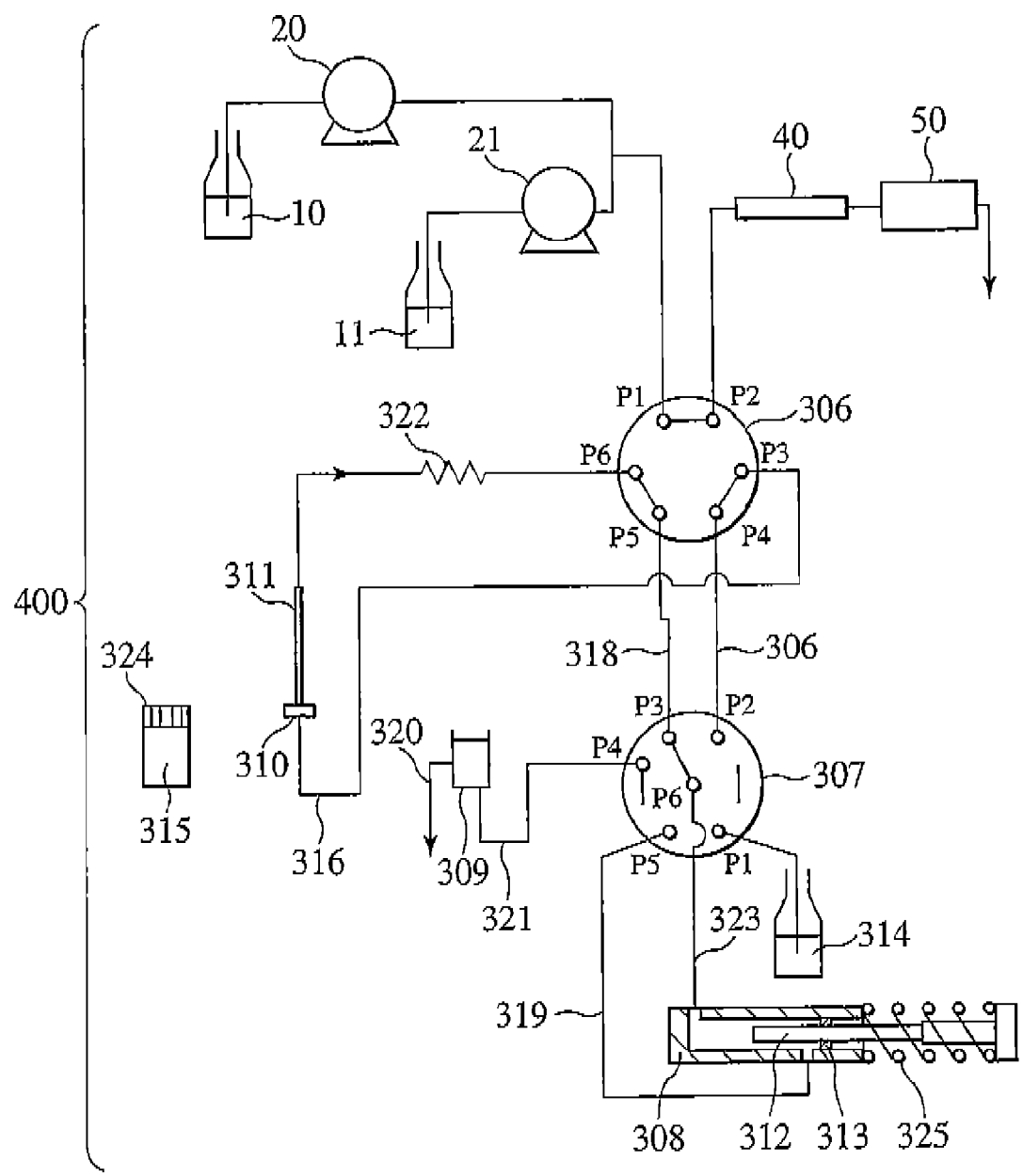
FIG. 4 is a diagram illustrating the structure of an automatic sampler and an example of the mechanical system operation thereof (at the time of waiting for injection of a sample) according to an embodiment of the present invention.
Figure 5:
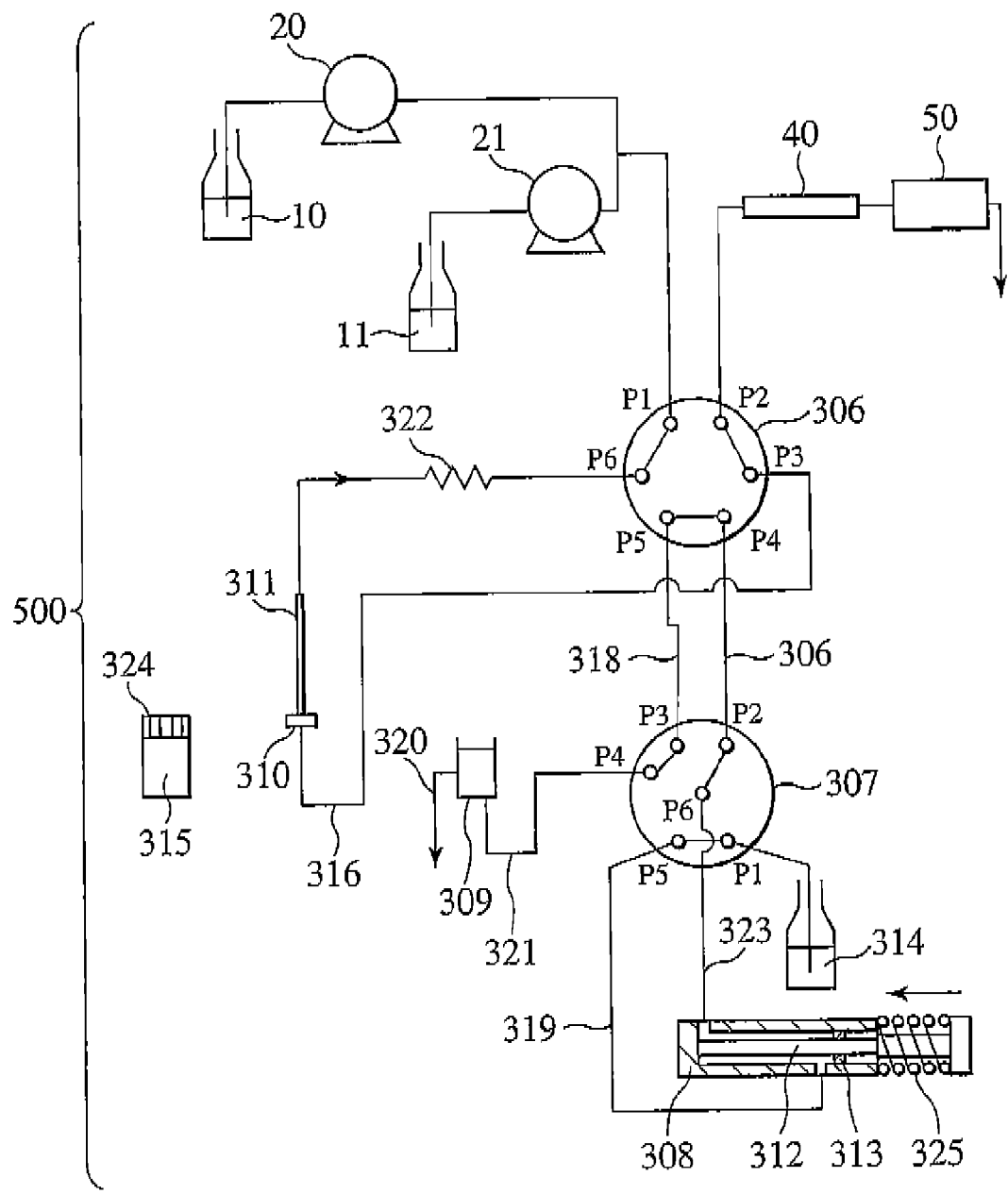
FIG. 5 is a diagram illustrating the structure of an automatic sampler and an example of the mechanical system operation thereof (at the time of injecting and measuring a sample) according to an embodiment of the present invention.

FIGS. 3, 4, 5 are diagrams each illustrating the sample introduction operation performed by the automatic sampler 30 of the liquid chromatography apparatus shown in FIG. 1.

FIG. 3 is a diagram illustrating the operation 300 of the automatic sampler 30 performed when a sample is sucked from a sample holding container 324. Eluent fed from the pumps A 20 and B 21 is ted into a column included in the column oven 40 through P1, P2 of a flow-path switching valve 306. A flow path is connected from a needle 311 inserted into the sample holding container 324 to a sample sucking syringe 308 through P6, P5 of the flow-path switching valve 306 and through P3, P6 of a flow-path switching valve 307. Movement of a plunger 312 disposed in the sample sucking syringe 308 to the sucking side causes the sample to be sucked into the needle 311 and a pipe 322.

FIG. 4 is a diagram illustrating a state 400 in which the automatic sampler 30 is waiting for the injection of a sample with the needle 311 moved to an injection port 310 after the sample sucking shown in FIG. 3. As is the case with the operation 300 performed at the time of sample sucking, eluent fed from the pumps A 20 and B 21 is fed to the column included in the column oven 40 through P1, P2 of the flow-path switching valve 306. A flow path is connected from the needle 311 to the sample sucking syringe 308 through P6, P5 of the flow-path switching valve 6 and through P3, P6 of the flow-path switching valve 307.

FIG. 5 is a diagram illustrating a state 500 in which the flow-path switching valves 306, 307 are switched from the state shown in FIG. 4 so as to introduce a sample into an analysis flow path. Eluent fed from the pumps A 20 and B 21 passes through P1, P6 of the flow-path switching valve 306. The eluent then passes through the pipe 322 holding a sample with the sample carried away by the eluent. The eluent further passes through the needle 311 and P3, P2 of the flow-path switching valve 306 so that the sample is introduced into a column included in the column oven 40.

On the other hand, the sample sucking syringe 308 becomes a flow path of P4, P5 of the flow-path switching valve 306, and is separated from the needle 311, so that individual operation including cleaning is possible.

Figure 6:
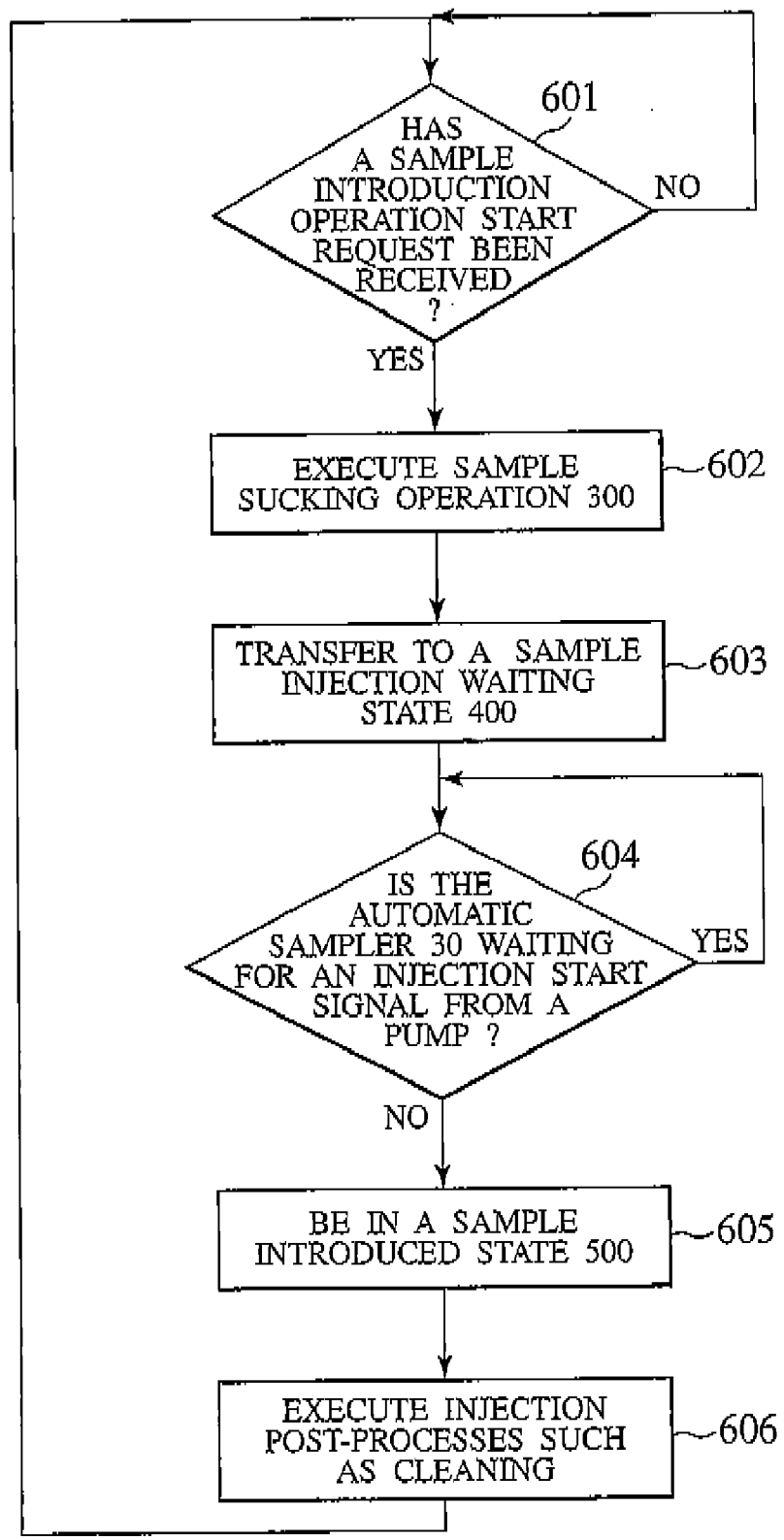
FIG. 6 is a flowchart illustrating an example of the injection operation of an automatic sampler, which is synchronized with a signal from a pump according to an embodiment of the present invention.

For the sample introduction operation of the automatic sampler 30, as shown in a flowchart of FIG. 6, a control program for the automatic sampler 30 is so programmed that each of the flow-path switching valves 306, 307 is switched by using a signal from the outside as a trigger. The switching in this case is an operation which transfers from the state 400 in which the automatic sampler 30 is waiting for the injection of the sample after sample sucking to the state 500 in which the sample has been introduced into the analysis flow path.

To be more specific, during the execution of waiting processing 601 that judges whether or not a sample introduction operation start request has been received, when a sample introduction operation start request is received (if it is judged to be "Yes" in the waiting processing 601 shown in FIG. 6), processing 602 is executed (more specifically, the sample sucking operation is executed), and processing 603 is then executed (more specifically, the automatic sampler 30 is brought into the sample injection waiting state 400). After that, waiting processing 604 is performed to judge whether or not a synchronization signal synchronized with a liquid feeding cycle occurring from the pump (an injection start signal from the pump) has been received. In the waiting processing 601 that judges whether or not a sample introduction operation start request has been received, if no sample introduction operation start request is received (that is, if it is judged to be "No" in the waiting processing 601 shown in FIG. 6), the processing 601 of judging whether or not a sample introduction operation start request has been received is repeated.

During the execution of the processing 604 that judges whether ox not the automatic sampler 30 is waiting for a synchronization signal synchronized with a liquid feeding cycle occurring from the pump (an injection start signal from the pump), when an injection start signal is received from the pump (that is, if it is judged to be "No" in the waiting processing 604 shown in FIG. 6), processing 605 of transferring to the sample introduced state 500 is executed (more specifically, on the receipt of a synchronization signal, the flow-path switching valves 306, 307 are switched to transfer to the state 500 in which the sample has been introduced into the analysis flow path). After that, processing 606 of executing injection post-processes (such as cleaning) is performed, before the process returns to the processing 601 that judges whether or not a sample introduction operation start request has been received. During the execution of the waiting processing 604 that judges whether or not the automatic sampler is waiting for a synchronization signal synchronized with a liquid feeding cycle occurring from the pump (an injection start signal from the pump), if no injection start signal is received from the pump (that is, if it is judged to be "Yes" in the waiting processing 604 shown in FIG. 6), the processing 604 of judging whether or not the automatic sampler is waiting for a synchronization signal synchronized with a liquid feeding cycle occurring from the pump (an injection start signal from the pump) is repeated.

Figure 7:
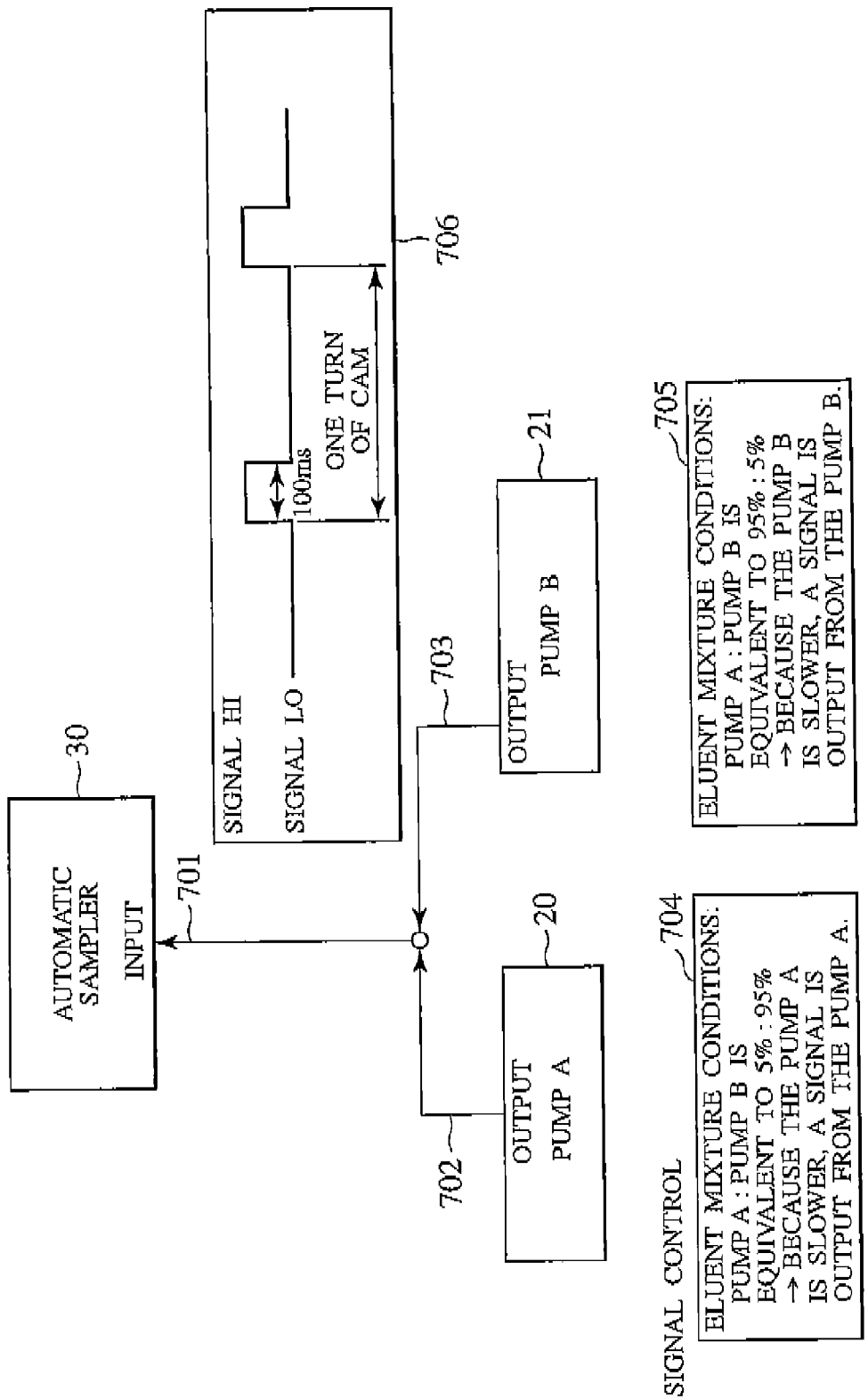
FIG. 7 is a diagram illustrating an example of signal cable connections among a pump A, a pump B, and an automatic sampler according to an embodiment of the present invention.

FIG. 7 is a diagram showing that the pump A 20, the pump B 21, and the automatic sampler 30 are connected to one another through special signal cables 701, 702, 703 that input/output a liquid feeding cycle signal of the pump. Each of the pumps A 20 and B 21 outputs a control signal, which is received by the automatic sampler 30.

In addition, as shown in a time chart 706 of FIG. 7, the pump shown in FIG. 2 is programmed by the control unit 208 as follows: detecting a cam position by the cam position detection sensor 215; and outputting a signal (for a period of time of a signal HI) at a position at which the cam rotates by a specified angle with respect to the cam position as the reference point.

As the synchronization signal output timing, one synchronization signal is output per liquid feeding cycle. The pump control unit 208 determines the rotational speed of the motor on the basis of given values of both the liquid feeding amount and a ratio of concentration. However, the pump control unit 208 is so programmed that only when the concentration at which own pump is to be controlled is lower than that for other pumps under the set control conditions, a control signal is transmitted.

For example, the signal control is performed as below. As indicated by reference numeral 704 in FIG. 7, if eluent mixture conditions are specified as follows: the pump A: the pump B is 5%:95%, the pump A is slower, and accordingly, a signal is output from the pump A. In contrast, as indicated by reference numeral 705 in FIG. 7, if eluent mixture conditions are specified as follows: the pump A: the pump B is 95%:5%, the pump B is slower, and accordingly, a signal is output from the pump B.

Figure 8:
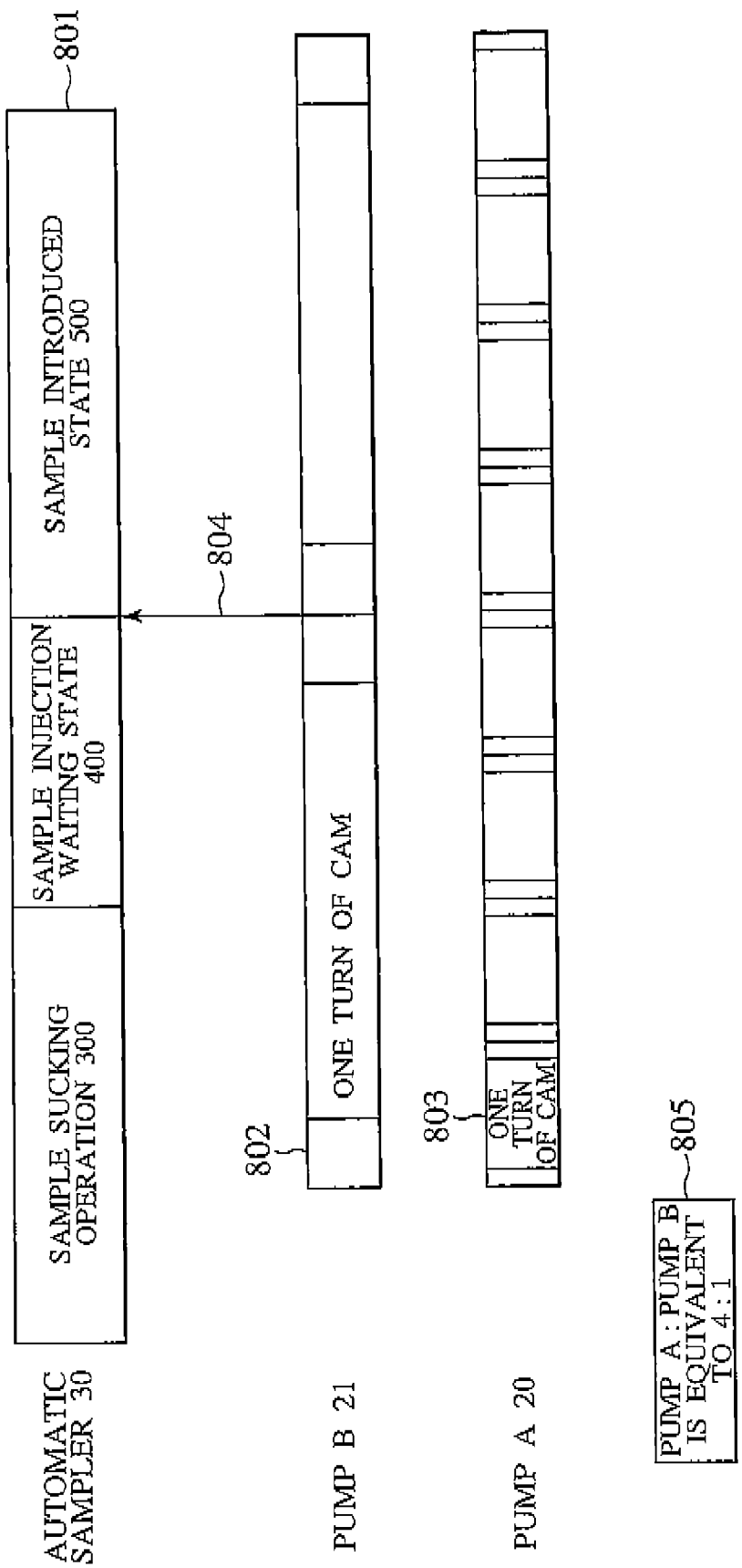
FIG. 8 is a timing chart illustrating, as an example, liquid feeding cycles of the pumps A and B, and the injection operation of an automatic sampler according to the embodiment of the present invention.

As shown in the timing chart of FIG. 8, under the sample introduction control based on a synchronization signal of the automatic sampler 30, and under the signal output control based on the connections among the pump A20, the pump B21, and the automatic sampler 30 in FIG. 7 through the signal cables, the automatic sampler 30 switches the flow-path switching valves 306, 307 by using, as a trigger, a signal 804 that is output from a pump whose sucking and discharge cycle is slower (the pump B21). Thus, the automatic sampler 30 transfers to the state 500 in which the sample has been introduced into the analysis flow path. Reference numeral 801 denotes a timing chart of the automatic sampler 30; reference numeral 802 denotes a timing chart of the pump B 21; and reference numeral 803 denotes a timing chart of the pump A 20.

In the example shown in FIG. 8, as indicated by reference numeral 805, a liquid-feeding-cycle speed ratio of the pump A 20 to the pump B 21 is equivalent to 4:1. Accordingly, the pump B 21 is slower than the pump A 20.

This embodiment describes only a control method that uses signal cables. However, the data processor 70 can communicate with the pump A 20, the pump B 21, and the automatic sampler 30. Such a communication function allows for control on specifying a pump that outputs information; inputting synchronization information from a pump; and requesting to the automatic sampler 30 to transfer to the state 500 in which a sample has been introduced into an analysis flow path. The control thus performed is equivalent to that when signal cables are used.

Second Embodiment

Figure 9:
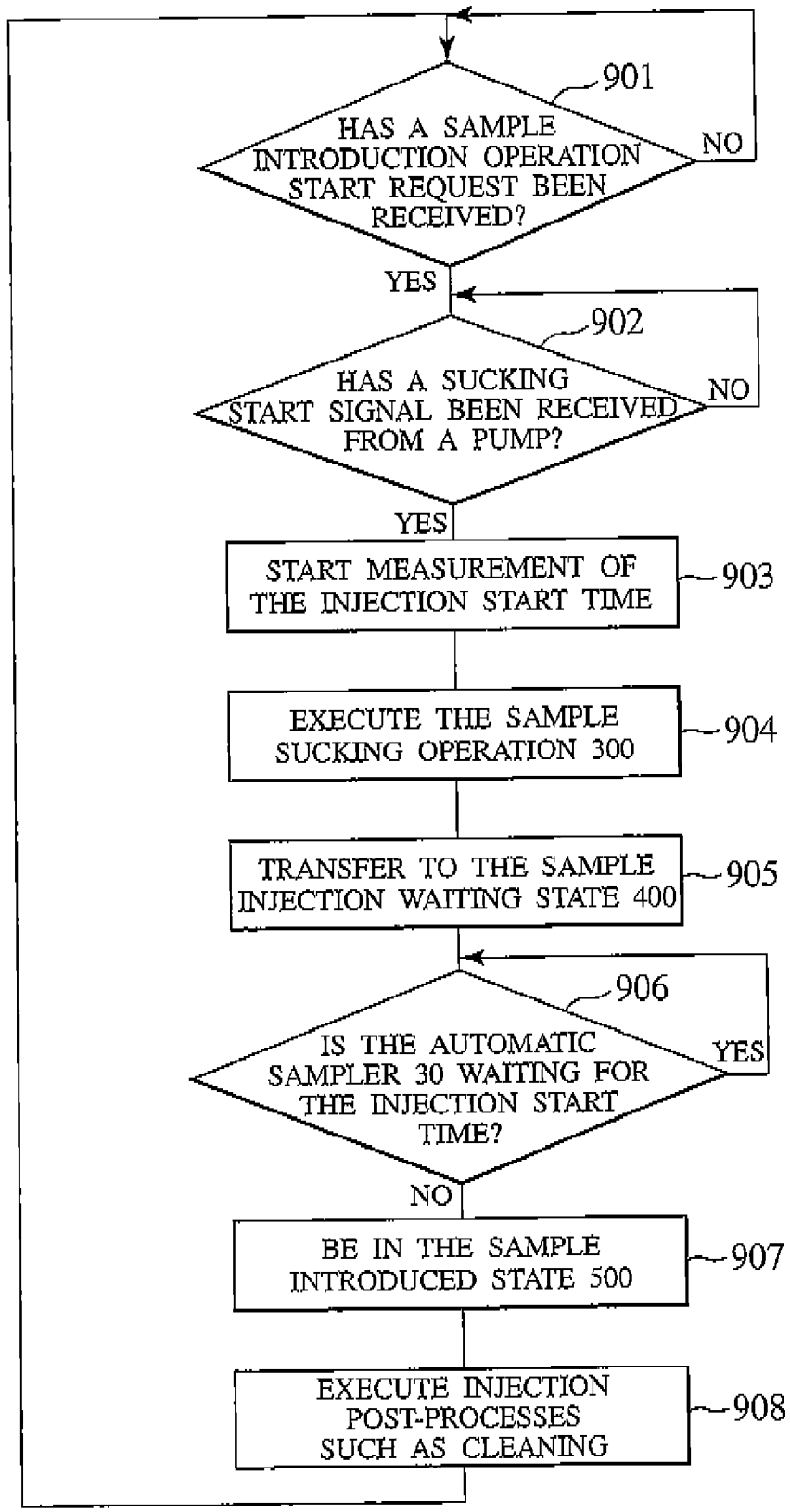
FIG. 9 is a flowchart illustrating an example of the sample sucking operation and the injection operation of an automatic sampler, which is synchronized with a signal from a pump according to an embodiment of the present invention.

For the sample introduction operation of the automatic sampler 30 in the liquid chromatography apparatus according to the first embodiment, the control program shown in the flowchart of FIG. 6 is changed such that the control program operates according to the flowchart of FIG. 9.

To be more specific, during the execution of waiting processing 901 that judges whether or not a sample introduction operation start request has been received, when a sample introduction operation start request is received (that is, if it is judged to be "Yes" in the waiting processing 901 shown in FIG. 9), the automatic sampler executes, instead of immediately starting the sample sucking operation, waiting processing 902 that judges whether or not a synchronization signal of a pump (a sucking start signal from the pump) has been received. If no sucking start signal is received from the pump (that is, if it is judged to be "No" in the waiting processing 901 shown in FIG. 9), the waiting processing 902 of judging whether or not a synchronization signal of the pump (a sucking start signal from the pump) has been received is repeated.

When a sucking start signal is received from the pump (that is, if it is judged to be "Yes" in the processing 902 shown in FIG. 9), the automatic sampler 30 executes processing 903 of starting measurement of the injection start time.

Then, after processing 904 of executing the sample sucking operation 300, processing 905 of transferring to the sample injection waiting state 400 is executed (more specifically, the processing 905 is processing that brings the automatic sampler into the state 400 in which the automatic sampler is waiting for injection of a sample with the needle 311 in FIG. 4 moved to the injection port 310 after the sample is sucked). After that, waiting processing 906 of judging whether or not the automatic sampler is waiting for the start time of sample injection from the pump is executed. In the waiting processing 906 that judges whether or not the automatic sampler is waiting for the start time of sample injection from the pump (more specifically, in processing of waiting for the injection start time whose measurement has been started in the processing 903), if the injection start time has arrived (that is, if it is judged to be "No" in the waiting processing 906 shown in FIG. 9), the valves 306, 307 are switched so as to execute processing 907 of transferring to the state 500 in which the sample has been introduced into the analysis flow path. After that, processing 908 of executing injection post-processes (such as cleaning) is performed, before the process returns to the processing 901 that judges whether or not a sample introduction operation start request has been received If the injection start time at which measurement has been started in the processing 903 has not arrived (that is, if it is judged to be "Yes" in the waiting processing 906 shown in FIG. 9), the waiting processing 906 of judging whether or not the automatic sampler is waiting for the start time of sample injection is repeated.

Figure 10:
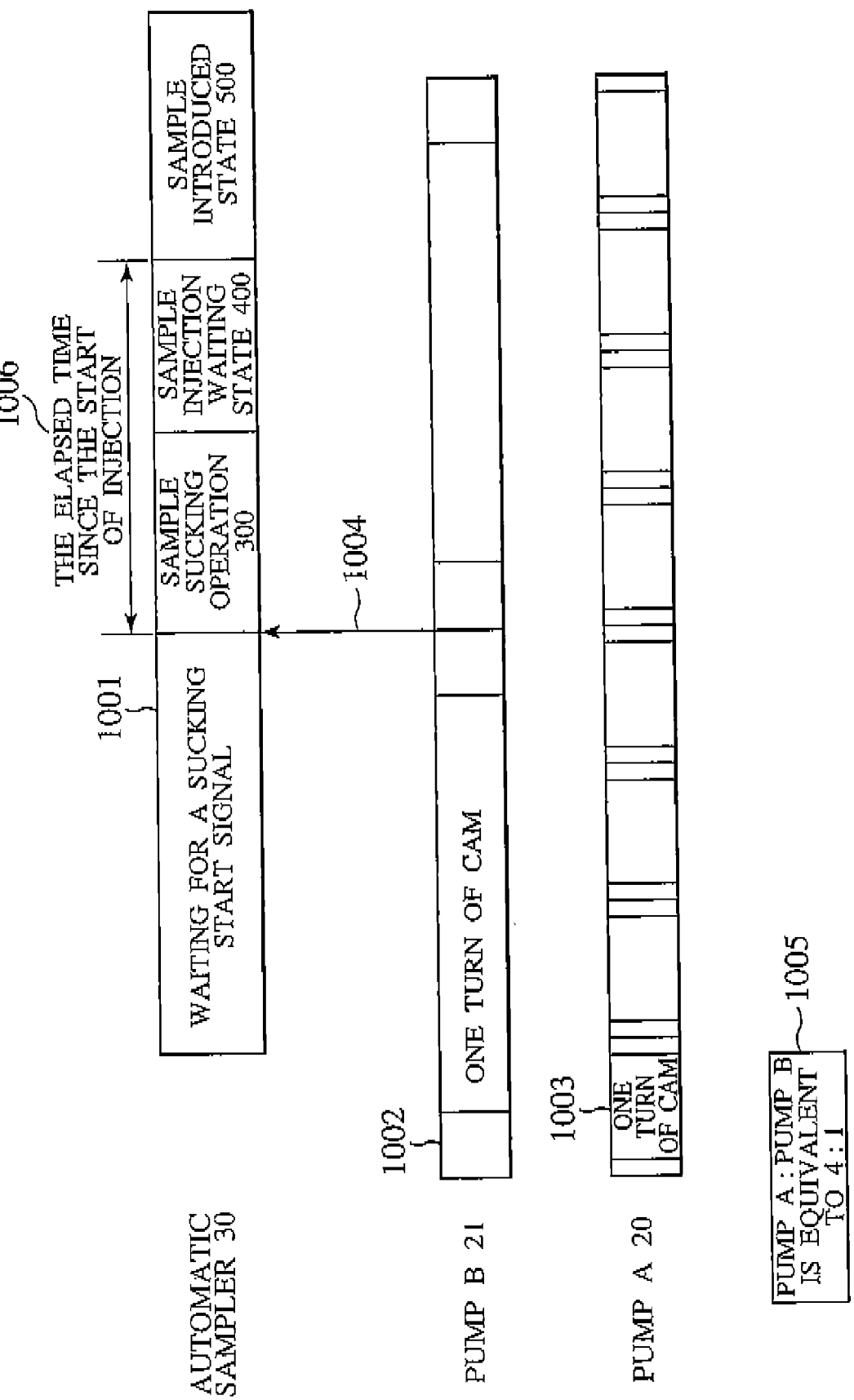
FIG. 10 is a timing chart illustrating, as an example, liquid feeding cycles of the pumps A and B, and the sample sucking operation and the injection operation of an automatic sampler according to an embodiment of the present invention.

As shown in the timing chart of FIG. 10, the automatic sampler 30 sucks a sample by using, as a trigger, a signal 1004 that is output from a pump whose sucking and discharge cycle is slower (the pump B 21). The automatic sampler 30 then switches the flow-path switching valves 306, 307 after a lapse of time synchronized with the signal (more specifically, after the time 1006 elapsed since the start of injection) so as to transfer to the state 500 in which the sample has been introduced into the analysis flow path. In the case of the sample sucking operation of the automatic sampler 30 shown in FIG. 3, when a sample is sucked, a nozzle 311 is required to move to a specified position of a vial 324, and to return to a position of the injection port 310 after the sample is sucked. Therefore, the time it takes to acquire a sample varies depending on a position of the vial 324. However, in this embodiment in which the flow-path switching valves 306, 307 are switched after a fixed period of time since the sample is sucked, the variation in time required for the automatic sampler 30 to suck the sample does not influence the synchronization with the pump. Reference numeral 1001 denotes a timing chart of the automatic sampler 30; reference numeral 1002 denotes a timing Chart of the pump B 21; and reference numeral 1003 denotes a timing chart of the pump A 20. In the example shown in FIG. 10, as indicated by reference numeral 1005, a liquid-feeding-cycle speed ratio of the pump A 20 to the pump B 21 is 4:1. Accordingly, the pump B 21 is slower than the pump A 20.

Third Embodiment

Figure 11:
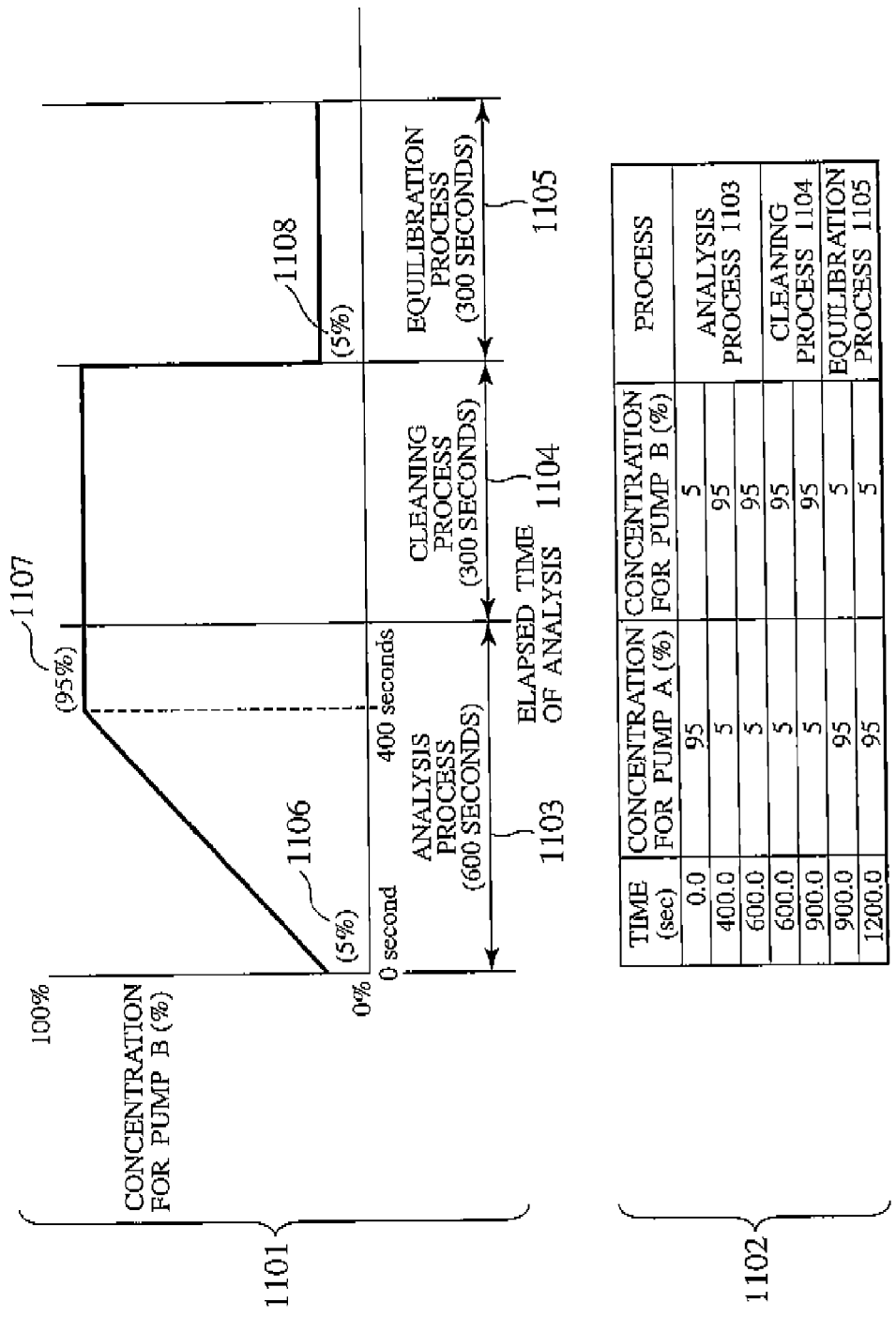
FIG. 11 illustrates an example of the concentration control according to an embodiment of the present invention.

FIG. 11 illustrates an example of general concentration control of analysis using "gradient" in the liquid chromatography apparatus according to the second embodiment. In the example, the speeds of the pumps A 20 and B 21 are changed during analysis, which causes the mixture concentration between the eluent A 10 and the eluent B 11 to change. The change in mixture concentration during the elapsed time of analysis is illustrated as a graph 1101. In the graph 1101, a vertical axis indicates the concentration for the pump B, whereas a horizontal axis indicates the elapsed time of analysis. The general concentration control during analysis includes an analysis process 1103, a cleaning process 1104, and an equilibration process 1105.

The analysis process 1103 is a process for gradually increasing up to the specified level the concentration of eluent composed of a constituent with which a sample is sufficiently eluted, and then for analyzing the separated constituent of the sample.

The cleaning process 1104 is a process for, after the analysis process 1103 is completed, discharging a residual sample in a column by feeding, at high concentration, eluent which allows the sample to be easily eluted.

The equilibration process 1105 is a process for, after the cleaning process 1104 is completed, filling a flow path with eluent whose concentration is the same as that at the start of measurement to bring the column and a piping flow path of the liquid chromatography apparatus into an initial state in which the next analysis can be made.

The concentration and time are determined based on, for example, the properties of eluent, the properties of a sample, the capacity of a column, the capacity of piping included in the liquid chromatography apparatus.

The control program for controlling the elapsed time of analysis and the mixture concentration of eluent is inputted and set in the data processor 70, the pump A 20, and the pump B 21 in a format of a time table 1102.

Figure 12:
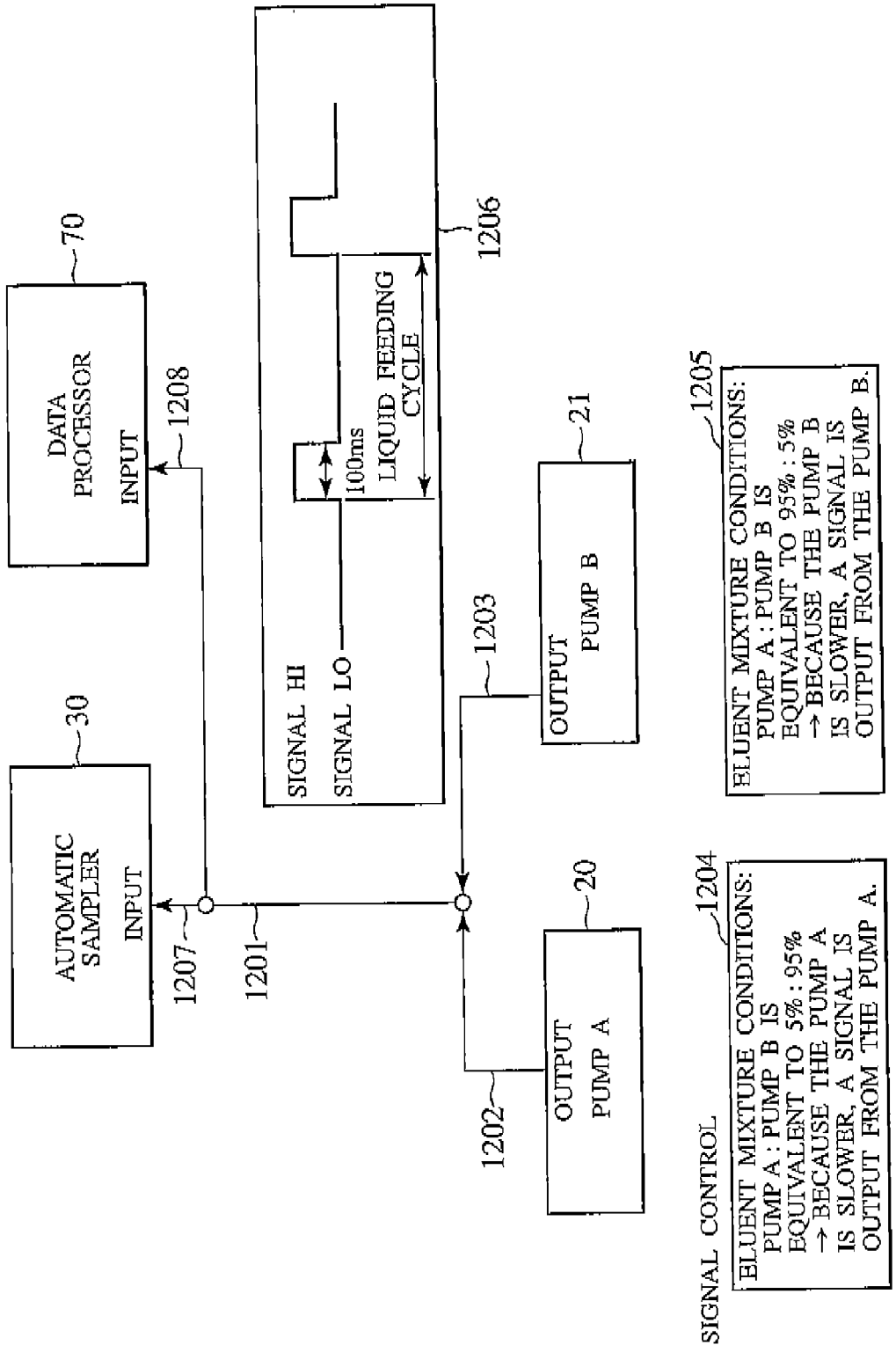
FIG. 12 is a diagram illustrating an example of signal cable connections among a pump A, a pump B, an automatic sampler, and a data processor according to an embodiment of the present invention.

In addition to the configuration shown in FIG. 7, a special signal cable 1208 is connected to the data processor 70 in FIG. 12 so that even the data processor 70 can detect a signal output from the pump. As is the case with FIG. 7, conditions under which a pump outputs a signal are as follows: a pump whose concentration is lower outputs a signal output (1204, 1205) on a liquid feeding cycle basis. How a signal HI is output is shown by reference numeral 1206.

Figure 13:
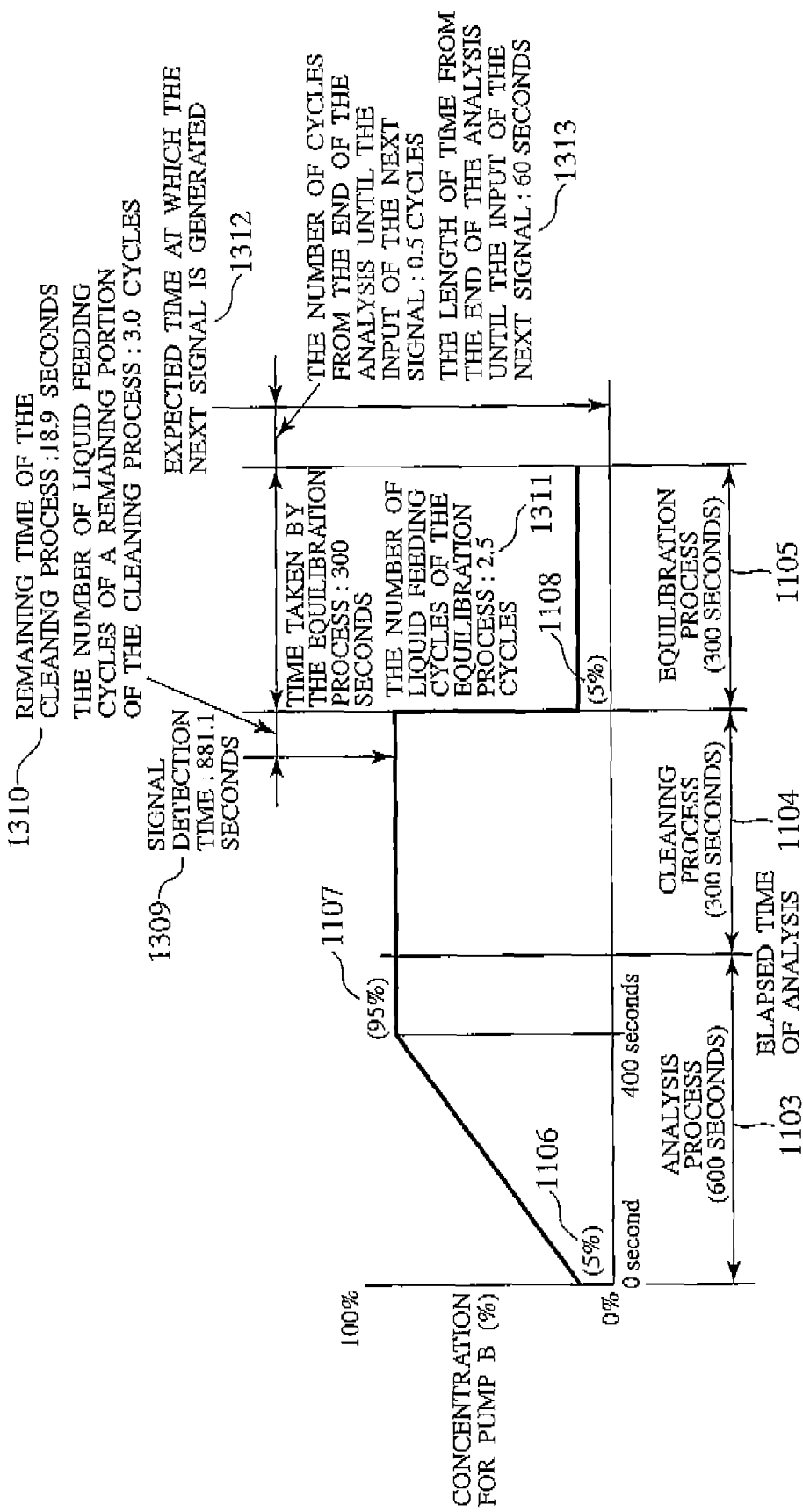
FIG. 13 is a chart illustrating an example of a liquid feeding process expected before the correction of the analysis time according to an embodiment of the present invention.

FIG. 13 is a chart illustrating the expected length of time 1313 taken from the end of analysis by a time program before the analysis time is corrected up to the time at which the pump outputs, for the next analysis, a synchronization signal 1312 used for the start of sucking into the automatic sampler 30. In the case of this control, the pump B 21 whose operation speed is slower at the start of the analysis generates a signal for synchronizing with the automatic sampler 30 at the start of sample sacking. In addition, as is the case with the first embodiment, as conditions required for calculation, one turn of the cam of the pump B 21 causes sucking and discharging whose amount corresponds to 100 µL; and the liquid feeding amount required for the analysis is 1000 µL/min.

When the pump B 21 feeds liquid at 5% in the equilibration process 1105, the length of time it takes for one cycle of liquid feeding is 120 seconds. When the pump B 21 feeds liquid at 95% in the cleaning process 1104, the length of time it takes for one cycle of liquid feeding is 120 seconds/19 cycles=6.3 seconds.

If a signal from the pump B 21 which is monitored by the data processor 70 is detected (1309) after a lapse of 881.1 seconds since the start of the analysis, the remaining time of the cleaning process 1104 and the number of liquid feeding cycles executed by a remaining portion of the cleaning process 1103 are determined by the following equations:

The remaining time of the cleaning process=900 seconds−881.1 seconds=18.9 seconds (reference numeral 1310)

The number of liquid feeding cycles of a remaining portion of the cleaning process=18.9 seconds/6.3 seconds=3.0 cycles (liquid feeding at 95%) (reference numeral 1310)

Because it takes 300 seconds in the equilibration process 1105, the number of liquid feeding cycles executed here is calculated as follow:

The number of liquid feeding cycles of the equilibration process=300 seconds/120 seconds=2.5 cycles (liquid feeding at 5%) (reference numeral 1311)

Therefore, at a point of time at which this analysis is completed, the liquid feeding cycle of the pump B 21 advances by 0.5 cycles, and accordingly, a signal is output after the progress by the remaining 0.5 cycles. As a result, the length of time from the end of the analysis until the input of the next sample sucking start signal can be expected by the following equation:

The length of time from the end of the analysis until the input of the next sample sucking start signal=0.5 cycles×120 seconds=60 seconds (reference numeral 1313)

Figure 14:
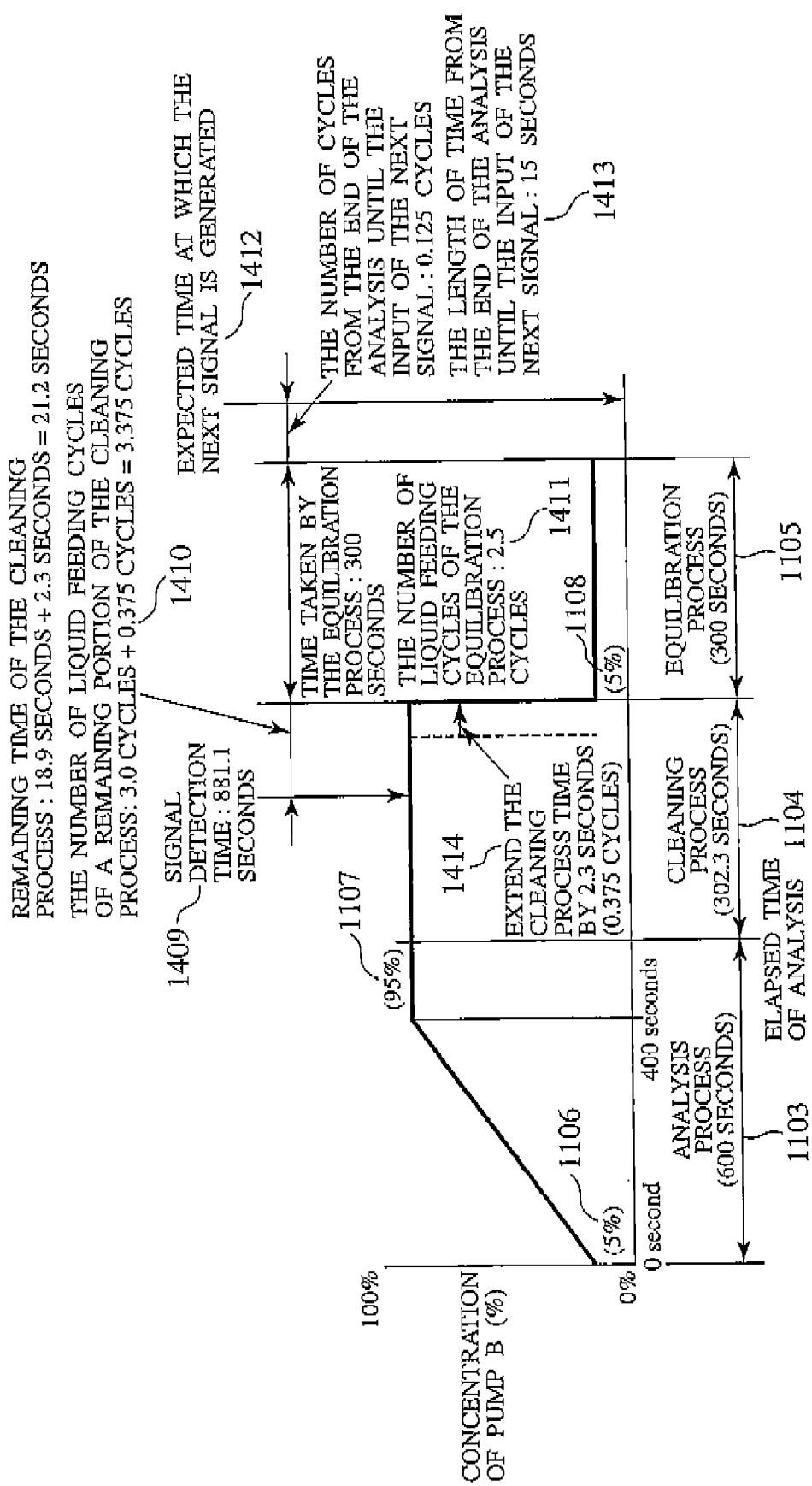
FIG. 14 is a chart illustrating an example of a liquid feeding process after the correction of the analysis time according to the embodiment of the present invention.

FIG. 14 is a chart illustrating processing of shortening the length of time from the end of the analysis until the input of the next sample sucking start synchronization signal to 15 seconds by adjusting the execution time of the cleaning process 1104 under the same conditions as those shown in FIG. 13.

The current expected length of time is 60 seconds. In order to shorten the current expected length of time to 15 seconds, the following calculation is performed:

The number of cycles which corresponds to 15 seconds=15 seconds/120 seconds=0.125 cycles (liquid feeding at 5%) (reference numeral 1413)

In order to end the analysis with 0.125 cycles remained, it is necessary to advance the liquid feeding cycle by 0.375 cycles in comparison with the liquid feeding cycle before adjustment. This is calculated by the following equation:

The remaining number of cycles before adjustment−the number of cycles to be left after adjustment=0.5−0.125=0.375 cycles This is adjusted by the cleaning process 1404 that feeds liquid at 95%. 0075

The cleaning process time to be adjusted (added)=0.375 cycles×6.3 seconds=2.36 seconds The remaining time of the cleaning process=18.9 seconds+2.3 seconds=21.2 seconds (reference numeral 1310)

The number of liquid feeding cycles of a remaining portion of the cleaning process=3 cycles+0.375 cycles=3.375 cycles (liquid feeding at 95%) (reference numeral 1410)

By extending the execution time (900 seconds) of the cleaning process 1404 by 2.3 seconds, the next sample sucking start signal is output after a lapse of about 15 seconds since the end of analysis (reference numeral 1413).

Figure 15:
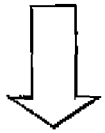
FIG. 15 illustrates an example of a time table after the correction of the analysis time according to the embodiment of the present invention.

FIG. 15 illustrates a time table 1502 in which the cleaning process 1404 is adjusted by 2.3 seconds. To be more specific, time settings after the last time 1503 of the cleaning process become longer by 2.3 seconds. The data processor 70 automatically updates the time table. The updated control information is set for the pump A 20 and the pump B 21 so that the control time of the cleaning process 1404 is changed. In addition, the updated time table is displayed, as new control conditions, on the output device 80 connected to the data processor 70.

Fourth Embodiment

In order to cope with a change in volume of solvent at the time of pressurization in a liquid chromatography apparatus according to the third embodiment, a pump that is subjected to pressurization/acceleration control is required to correct the calculation of the third embodiment by actually measured values.

FIG. 16 is a chart illustrating processing to be performed when a correction is made. If the data processor 70 detects a signal from a pump at 875.43 seconds (reference numeral 1614) and at 881.1 seconds (reference numeral 1609) in the cleaning process 1604, the execution time of one liquid feeding cycle of the pump B21 is calculated as follow:

The execution time of one liquid feeding cycle=881.1 seconds−875.43 seconds=5.67 seconds (reference numeral 1615)

Thus, signals from the pump B21, which should be output at intervals of 6.3 seconds, are output at intervals of 5.67 seconds.

In this case, a correction coefficient of the operation speed is calculated as follows:

Correction coefficient=5.67/6.3=0.9

The remaining time of the cleaning process=900 seconds−881.1 seconds=18.9 seconds The number of liquid feeding cycles of a remaining portion of the cleaning process=18.9 seconds/(6.3 seconds×0.9)=3.3 cycles (liquid feeding at 95%)

The number of liquid feeding cycles of the equilibration process=300 seconds/(120 seconds×0.9)=2.8 cycles (liquid feeding at 5%) (reference numeral 1611)

Liquid feeding cycle position at the end of analysis=3.3+2.8=6.1→0.1 cycles

Based on this expectation, because the liquid feeding cycle position advances by 0.1 cycles at the end of analysis, a signal is output after the liquid feeding cycle of the pump B21 advances by remaining 0.9 cycles. Therefore, the length of time from the end of the analysis until the input of the next sample sucking start signal can be expected by the following equation:

The length of time from the end of the analysis until the input of the next sample sucking start signal=0.9 cycles×(120 seconds×0.9)=97.2 seconds In order to change the above 97.2 seconds to 15 seconds, the number of cycles after the end of analysis is calculated as follows:

The number of cycles which corresponds to 15 seconds=15 seconds/(120 seconds×0.9)=0.139 cycles (liquid feeding at 5%) (reference numeral 1613)

The remaining number of cycles before adjustment−the number of cycles to be left after adjustment=0.9−0.139=0.761 cycles The execution time of the cleaning process 1604 is adjusted by 0.761 cycles.

The cleaning process time to be adjusted (added)=0.761 cycles×(6.3 seconds×0.9)=4.31 seconds The remaining time of the cleaning process=18.9 seconds+4.3 seconds=23.2 seconds The number of liquid feeding cycles of a remaining portion of the cleaning process=3.3 cycles+0.761 cycles=4.061 cycles (liquid feeding at 95%) (reference numeral 1610).

By extending the execution time (900 seconds) of the cleaning process 1604 by 4.3 seconds, the next sample sucking start signal is output after a lapse of about 15 seconds since the end of analysis (reference numeral 1613).

FIG. 17 illustrates a time table in which the cleaning process 1604 is adjusted by 4.3 seconds.

To be more specific, time settings after the last time 1703 of the cleaning process become longer by 4.3 seconds.

The data processor 70 automatically updates the time table. The updated control information is set for the pumps A 20 and B 21 so that the control time after the cleaning process 1703 is changed.

On the assumption that if the liquid feeding pressure is substantially constant for the liquid feeding amount, the volume to be pressurized and accelerated is also constant, a coefficient of the cycle time acquired from a signal of the cleaning process 1604 is also used in the equilibration process 1105. Moreover, further accuracy can be attained by separately acquiring a coefficient on the basis of a signal inputted from a pump under the same conditions as those of the equilibration process 1105, and then by calculating the number of times the operation is performed in the equilibration process 1105.

According to the embodiments of the present invention, for example, in order to improve the accuracy in analysis repeatability of a liquid chromatography apparatus that feeds different eluent by use of a plurality of pumps and achieves the mixture of eluent, each of the pumps includes means for notifying an automatic sampler and a higher-level control unit that the specified timing of a liquid feeding cycle is reached. With the configuration as above described, a pump whose liquid feeding cycle is the slowest transmits own information so that analysis is synchronized with a liquid feeding cycle. Moreover, a cycle position of a liquid feeding cycle at the end of analysis is expected; and the analysis time is automatically adjusted so that the wait time until the start of the next analysis becomes the shortest.

While the invention has been described in its preferred embodiments, it is to be understood that the words which have been used are words of description rather than limitation and that changes within the purview of the appended claims may be made without departing from the true scope and spirit of the invention in its broader aspects.

What is claimed is:

1. A liquid chromatography apparatus comprising:
   a sample syringe; and
   a plurality of pumps, each configured to feed eluent; and
   a separation column;
   wherein the liquid chromatography apparatus is configured to mix, at a mixing point using a pressure, a plurality of eluents received from the plurality of pumps, thereby resulting in a mixed eluent;
   wherein the liquid chromatography apparatus is configured to feed the mixed eluent through the sample into the separation column, at the same pressure as the mixing point; and
   wherein the liquid chromatography apparatus is configured to synchronize a sample injection operation with a phase of a control process for a pump whose flow speed at the time of sample injection is slowest of the plurality of pumps.

2. The liquid chromatography apparatus according to claim 1,
   wherein when the liquid chromatography apparatus executes an injection process twice or more, the liquid chromatography apparatus is configured to synchronize the length of time between first injection operation and second injection operation with (1) one cycle time of pump control for the synchronization, or (2) the total length of time of a plurality of cycles.

3. A liquid chromatography apparatus comprising:
   a plurality of liquid-chromatograph liquid feeding units configured to mix eluent, each of which differs in speed from the others;
   wherein the liquid chromatography apparatus is configured to mix, at a mixing point using a pressure, a plurality of eluents received from the plurality of liquid-chromatograph liquid feeding units, thereby resulting in a mixed eluent;
   wherein the liquid chromatography apparatus is configured to feed the mixed eluent through the sample syringe into a separation column, at the same pressure as at the mixing point; and
   wherein the liquid chromatography apparatus is configured to generate a signal for instructing injection of a sample, in synchronization with a liquid feeding unit whose liquid feeding cycle is the slowest of the plurality of liquid feeding units.

4. The liquid chromatography apparatus according to claim 3,
   wherein the liquid chromatography apparatus is configured to adjust analysis time for a liquid feeding cycle so that a signal for the analysis time occurs at intervals of a specified period of time.

5. The liquid chromatography apparatus according to claim 4,
   wherein the specified period of time is set such that a signal for the analysis time always occurs at a same timing.

6. A liquid chromatography analysis method, comprising:
   mixing, at a mixing point using a pressure, a plurality of eluents received from a plurality of pumps, thereby resulting in a mixed eluent;
   feeding the mixed eluent through the sample syringe into a separation column, at the same pressure as the mixing point; and
   synchronizing a sample injection operation with a phase of a control process for a pump whose flow speed at the time of sample injection is slowest of the plurality of pumps.

7. The liquid chromatography analysis method according to claim 6, further comprising the step of:
   when an injection process is executed twice or more, synchronizing the length of time between a first injection operation and a second injection operation (1) one cycle time of pump control for the synchronization, or (2) the total length of time of a plurality of cycles.

8. A liquid chromatography analysis method, comprising:
   mixing, at a mixing point using a pressure, eluent received from a plurality of liquid-chromatograph liquid feeding units, thereby resulting in a mixed eluent, wherein each liquid-chromatograph liquid feeding unit differs in speed from the others;
   feeding the mixed eluent into a separation column, at the same pressure as at the mixing point; and
   instructing a sample injection, in synchronization with a liquid feeding unit whose liquid feeding cycle is the slowest of the plurality of liquid feeding units.

9. The liquid chromatography analysis method, according to claim 8,
   wherein the analysis time for a liquid feeding cycle is adjusted so that an operation of instructing sample injection for the analysis time occurs at intervals of a specified period of time.

10. The liquid chromatography analysis method according to claim 9,
    wherein the specified period of time is set such that a signal for the analysis time always occurs in a same timing.

* * * * *